United States Patent [19]

Sweeney et al.

[11] Patent Number: 4,986,655

[45] Date of Patent: Jan. 22, 1991

[54] APPARATUS FOR MEASURING DIFFUSE ATTENUATION COEFFICIENT OF SEA WATER

[75] Inventors: Harold E. Sweeney, Menlo Park; Paul J. Titterton, Palo Alto; Donald A. Leonard, Cupertino, all of Calif.

[73] Assignee: GTE Government Systems Corporation, Stamford, Conn.

[21] Appl. No.: 443,620

[22] Filed: Nov. 30, 1989

[51] Int. Cl.$^5$ ........................ G01N 21/00; G01J 3/44
[52] U.S. Cl. ...................................... 356/73; 356/301
[58] Field of Search ........................... 356/301, 43, 73; 250/574

[56] References Cited

U.S. PATENT DOCUMENTS

| 4,123,160 | 10/1978 | Caputo et al. | 356/75 |
| 4,411,525 | 10/1983 | Ogawa | 356/318 |
| 4,867,558 | 9/1989 | Leonard et al. | 356/349 |

FOREIGN PATENT DOCUMENTS 2150283A 6/1985 United Kingdom .................. 356/73

OTHER PUBLICATIONS

Atomic Resonance Filters, Gelbwachs, IEEE, 4/29/87, pp. 1266–1277.
Nato Advisory Group for Aerospace Research and Development, Austin et al., 4/10/81, pp. 18-1-18-9.
Iodine Filter in Raman and Brillouin Spectroscopy, Schoen et al., J. Phy. E. Sci. Inst, 6/72, pp. 509–512.
Computer Control of Raman & Brillouin Spectrometers, Rowell et al., Proceedings of the VIIIth International Conference on Raman Spectra., 1980, pp. 444–445.
"Brillouin Scattering in Water: The Landau–Placzek Ratio" by C. L. O'Connor, J. P. Schlept, *Journal of Chemical Physics*, vol. 47, No. 1, Jul. 1, 67, pp. 31–38.
"Atomic Resonance Filters" by J. A. Gelbwachs, *IEEE Journal of Quantum Physics*, vol. 24, No. 7, Jul. 1988, pp. 1266–1277.
"Remote Sensing of the Diffuse Attenuation Coefficient of Ocean Water" by R. W. Austin, *Special Topics in Optical Propagation*, AGARD Conference Proceedings, No. 300, pp. 18-1 and 18-9.
"Spectral Dependence of the Diffuse Attenuation Co-Efficient of Light in Ocean Waters" by R. W. Austin, T. J. Petzoid, *Optical Engineering*, Mar. 1986, vol. 25, No. 3, pp. 471–479.
"Optical Properties of the Clearest Natural Waters (200–800 nm)" by Raymond C. Smith, Karen S. Baker, *Applied Optics*, Jan. 15, 1981, vol. 20, No. 2, pp. 177–184.

*Primary Examiner*—F. L. Evans
*Assistant Examiner*—K. P. Hantis
*Attorney, Agent, or Firm*—Douglas M. Gilbert; John F. Lawler

[57] ABSTRACT

Apparatus is disclosed for remotely measuring the diffuse attenuation coefficient K of ocean water from a platform such as an aircraft flying over the ocean. A pulsed laser beam is directed as a probe beam from the aircraft into the water to produce therein Brillouin backscattering signals which emanate back up through the water to the aircraft. An optical receiver in the aircraft receives and processes those backscattered signals. A very narrow optical bandpass filter passes the Brillouin signals to a photodetector, a digitizer and a data processor, the latter being programmed to compute the diffuse attenuation coefficient at predetermined depths and at the Brillouin wavelength. Measurements of the diffuse attenuation coefficient at various depths is accomplished by sampling and digitizing the Brillouin signals at predetermined intervals, each interval corresponding to a depth beneath the surface of the water. A preferred embodiment of the invention features similar apparatus having two signal-processing channels for simultaneously deriving the diffuse attenuation coefficient at two wavelengths by analyzing the upwelling Brillouin (blue) and Raman (green) backscatter generated by the probe beam. An alternate embodiment of the invention features apparatus for measuring the diffuse attenuation coefficient K of ocean water from a submerged submarine.

16 Claims, 7 Drawing Sheets

APPARATUS FOR MEASURING DIFFUSE ATTENUATION COEFFICIENT OF SEA WATER

CROSS-REFERENCES TO RELATED APPLICATIONS

This patent application is generally related to the following patent application which was filed on the same date and assigned to the same assignee by the same inventors: "Method of Remotely Measuring Diffuse Attenuation Coefficient of Sea Water," Ser. No. 443,679.

BACKGROUND OF THE INVENTION

1. Field of the Invention

The present invention relates to the measurement of optical properties of sea water and more particularly to improved apparatus for remotely measuring the diffuse attenuation coefficient of light in sea water from an airborne platform such as an aircraft or alternatively from a surface vessel or a submerged platform.

2. Description of the Prior Art

The optical properties of water have been of scientific interest for centuries. A number of recent theoretical and experimental studies have been conducted to investigate and better characterize the optical diffuse attenuation coefficient, K, of both fresh and sea water. The diffuse attenuation coefficient of light in water is significant in a variety of problems associated with the optical transmission qualities of sea water. For example, the performance of aircraft-to-submarine laser communications is critically dependent upon the optical transmission properties of ocean water. Other electro-optical systems used in sub-surface ocean applications are: laser radar for bathymetry hard target detection and surveillance, lidar for temperature and salinity measurements and various optical imaging systems. Each application has a strong performance dependence on the optical clarity/attenuation of sea water.

The optical clarity of water or more precisely the transmission of optical energy in water is generally characterized by an exponential decay as a function of depth, i.e., $$I/I_o = \exp[-Kd] \quad (1)$$

where
I is the intensity of light after traveling through water to a depth d;
$I_o$ is the initial light intensity just beneath or at the water surface;
K is the diffuse attenuation coefficient at a single wavelength, and
d is water depth at the point of measurement.

Expression (1) characterizes the diffuse attenuation coefficient of water only at a single wavelength $\lambda$, since $K = f(\lambda)$. The value of K at a particular wavelength also varies widely with the geographical location of the testing area. For example, clear tropical ocean waters may have transmission windows with values of K as low as 0.02 $m^{<1}$ at blue wavelengths i.e., (400–460 nm). Whereas, cooler ocean waters and coastal waters in general have transmission windows with higher values of K that may be as great as 0.2 m or larger throughout the blue-green part of the spectrum i.e. (400–560 nm). Ocean currents, weather and seasonal variations also affect the value of K even at a given location in the ocean. Thus, the value of K is highly variable with time and with ocean depth.

The current data base of ocean K measurements is not adequate for producing accurate statistical results to develop arithmetic means, standard deviations and cumulative probability distributions. It is apparent that the existing data base of ocean K measurements must be greatly expanded if better electro-optical system modeling and performance estimates are to be made.

Existing apparatus and techniques for measuring K have severe limitations. Hide area coverage is obtained by satellite measurements that utilize the coastal zone color scanner (CZCS). This remote technique analyzes the color distribution of reflected and upwelling ambient sunlight from ocean water (and from atmospheric radiance) and infers values of K by means of an analysis of the observed color distribution. This technique is however limited to relatively shallow depths of the order of (1/K) that is, to a depth of 20 m if K=0.05 $m^{-1}$, and because of the remoteness of the satellite, its lateral spatial resolution is necessarily limited to approximately 800 m.

More direct measurement systems use photometers that are physically placed in the water and compare the intensity of sunlight as a function of depth with that obtained at the surface with a similar photometer. Such direct methods are inherently slow in generating data, require considerable manpower and are prone to inaccuracies resulting from changes in environmental conditions at the measuring location. Further such manual techniques are not suitable for rapidly and repeatedly gathering data over wide areas of the ocean and thus have limited utility.

The most venerable available device for directly measuring K is known as the Secchi disc and is described in "The Oceans" (Prentice-Hall, Englewood Cliffs, N.J.) 1982, at page 82. Basically, the Secchi disc is a round white disc 30 cm in diameter. The visibility of the disc, as seen by a human observer as it is lowered into a sunlit sea, is the measurement parameter. The depth at which the disc becomes indistinguishable is related to the value of K by the formula K=1.7/d, where d is the maximum depth of visibility in meters. This relationship varies from place to place from season to season and is highly empirical. Like the satellite measurements, this technique is limited to relatively shallow depths in the order of (1/K). Also, such techniques are manpower limited suggesting that an extensive worldwide survey would be too expensive to be practical. Moreover, relating this inferred K to a K at a specific wavelength is not a settled scientific issue.

This invention is directed toward improved apparatus for remotely measuring the diffuse attenuation coefficient which overcomes the above disadvantages.

OBJECTS AND SUMMARY OF THE INVENTION

A general object of the invention is the provision of diffuse attenuation coefficient measuring apparatus which is fast, accurate and reliable.

A further object is the provision of such apparatus which is capable of rapidly measuring the diffuse attenuation coefficient of ocean waters over wide areas including beneath the polar ice cap.

Still another object is the provision of such apparatus which is capable of directly measuring the diffuse attenuation coefficient at substantial and varying depths.

A further object is the provision of such apparatus which is useable in inhospitable areas or seasons unsuitable for surface ship operation.

Another object is the provision of such apparatus which permits measurement of the diffuse attenuation coefficient at two selected wavelengths simultaneously.

These and other advances in the art are achieved with apparatus for generating a pulsed laser beam which is directed as an optical probe beam into the water of interest. As the pulsed laser beam enters and propagates through the water, it generates among other things Brillouin and Raman backscattering at wavelengths different from the probe beam. An optical receiver positioned above the water surface collects and analyzes these optically backscattered signals. By comparing the intensities of these signals at various depths, associated processing equipment computes the diffuse attenuation coefficient, K, at any depth from which the scattering is generated. Brillouin and Raman scattering are very suitable for this purpose because they are intrinsic processes of the water itself, and the scattering cross section of the Brillouin and Raman scattering is independent of the particulate loading of the water.

In another aspect of the invention, optical transmitter and receiver apparatus is carried by a submerged platform to measure the diffuse attenuation coefficient of ocean waters above and below the platform by detecting and analyzing the same optical backscattering signals from Brillouin or Raman scattering or from both. The advantage of this alternative application is that it can measure values of K at much greater ocean depths than is possible with surface or airborne platforms, and it is possible to measure values of K in the Arctic Ocean below the polar ice cap, neither of which can be performed with conventional above-surface measurement techniques.

BRIEF DESCRIPTION OF THE DRAWINGS

For a better understanding of the invention as well as other objects and further features thereof, reference is made to the following description which is to be read in conjunction with the accompanying drawings wherein.

DESCRIPTION OF PREFERRED EMBODIMENTS

Figure 1:
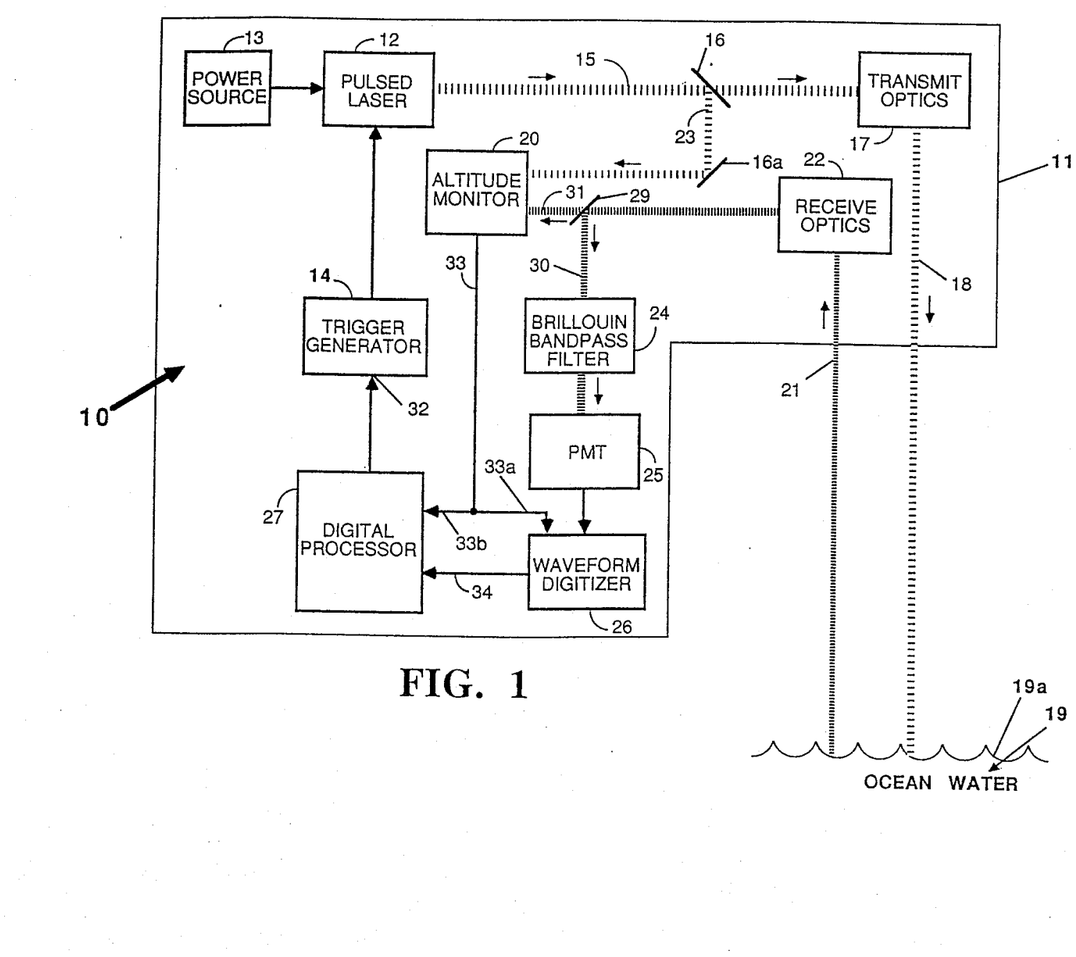
FIG. 1 is a schematic block diagram of apparatus embodying the invention.

Referring now to the drawings, FIG. 1 shows apparatus 10 embodying the invention using Brillouin scattering and mounted on an airborne platform, such as an aircraft, indicated by enclosure 11. Apparatus 10 comprises a pulsed laser 12, such as a frequency-doubled neodymium yittrium-aluminum-garnet (Nd:YAG) laser, energized by a power source 13 (such as an electric generator) and activated by a trigger generator 14. Pulsed output beam 15 has a nominal wavelength of 532 nm (green) with a nominal output power of one Joule per pulse. The linewidth of the laser output beam 15 should be comparable to or less than the Brillouin scattering linewidth, i.e., 0.0004 nm, for highest performance. Most of laser Output 15 passes through a partially transmissive mirror 16 to transmitter optics 17 which directs the laser pulses as a probe beam 18 into ocean water 19 being measured. Part of laser output 15 is reflected by mirror 16 to an altitude monitor 20.

The pulsed probe beam 18 at the 532 nm wavelength interacts with ocean water 19 and produces among other things, Brillouin scattering signals some of which propagate backwardly, i.e., in a direction opposite to that of the probe beam as indicated by return beam 21. Brillouin scattering is an intrinsic wavelength-shifting phenomenon of the water and is described in more detail in "Brillouin Scattering in Water: the Landau-Placzek Ratio," by C. L. O'Connor, J. P. Schlepf, J. Chem. Physics. Vol. 47, No. 1, 1 July 67. Such optical Brillouin signals 21 are received by receiver optics 22 (lenses, collection mirrors, etc.) of apparatus 10. Since the Brillouin signals that are produced in the water propagate into $4\pi$ steradians, transmitter optics 17 and receiver optics 22 need not necessarily be co-linear but merely have a common field of view of the ocean surface 19a. A portion of the output from receiver optics 22 passes through partially reflective mirror 29 to a second input of altitude monitor 20. Partially reflective mirror 29 reflects a portion of optical beam 30 to an extremely narrow optical bandpass filter 24 having a center wavelength shifted from the laser probe wavelength by only 0.006 nm. The purpose of filter 24 is to select at least one of the return Brillouin signals and reject the ambient light which includes other backscatter components and light reflected off the ocean surface 19a, i.e. sunlight and the probe beam itself. By way of example, filter 24 may include a narrowband interference filter for prefiltering of beam 30. Greater selectivity may be obtained by a Fabry-Perot interferometer. Alternatively, if pulsed laser 12 is a tunable laser such as a Titanium-Sapphire model that can be tuned to a 455.6608 nm wavelength, then greater selectivity may be obtained using an atomic resonance absorption filter with cesium gas as a component. Both techniques are described infra.

The filtered Brillouin signals are passed to a photomultiplier tube (PMT) 25 for conversion to an equivalent analog electrical signal. PMT 25 should have a bi-alkali photocathode for maximum quantum efficiency at the blue and green wavelengths and typically may be a Hamamatsu model R1924 PMT. The analog output signal is periodically digitized by waveform digitizer 26, and its digitized output 34 is further processed by a digital data processor 27. Digitizer 26 may be a waveform digitizer Tektronix model RTD 710A, and processor 27 may be a Hewlett-Packard technical computer system Model 9000 series 800.

In operation, receiver optics 22 collects the upwelling optical energy 21 consisting of reflected sunlight, the reflected probe beam, the backscattered energy and other extraneous light all of which is primarily directed by mirror 29 to a Brillouin bandpass filter 24. A portion of the received light 21 is diverted by partially reflective mirror 29 to a second input of altitude monitor 20. Altitude monitor 20 derives the altitude of platform 11 above the ocean surface 19a by comparing the difference in time between each output pulse from beam 15 and the receipt time of the associated laser pulse from the ocean surface 19a. Monitor 20 typically is a Hamamatsu model R1924 PMT coupled to a Fluke counter/timer Model PM6652C operating in a time interval mode. Altitude monitor 20 serves several functions related to the timing of the collected backscatter signals and to the computation of K values. At the very start of each collected pulse 21, altitude monitor 20 computes the altitude (H) above the water based upon the transit times of the outgoing (18) and incoming (21) pulses and then feeds this data to processor 27 for use in computing values of K. In addition altitude monitor 20 sends a start pulse to trigger digitizer 26, via path 33a (trigger in), and to trigger processor 27, via path 33b, at the very start of each collected pulse 21 As will be explained in greater detail below, these trigger pulses provide processor 27 with a reference for the start of each series of bytes coming from digitizer 26 which represent intensity values of Brillouin scattering generated from incremental ocean depths. The timing cycle is initiated by an input indicated at 32 to trigger generator 14 from processor 27. Processor 27 can be set to cause generator 14 to fire laser 12 at some regular interval, such as 100 pulses per second (pps), or it can increase the pulse rate to the maximum rate the processor can handle by signalling trigger generator 14 when the former has almost finished processing of the previous set of digitized samples. As a practical matter fine tuning of the system may be necessary if the delays through filter 24 and PMT 25 are significantly greater than the delay through monitor 20.

The determination of ocean depth at which the diffuse attenuation coefficient measurements are made is a matter of timing the return backscatter signals. Waveform digitizer 26 is normally set to digitize the incoming analog signal from PMT 25 at regular timing intervals, e.g. every 25 ns. By triggering digitizer 26 to begin its sampling and digitization on the leading edge of each Brillouin pulse, the initial sample will correspond to the Brillouin backscatter generated at the ocean surface or just below, i.e., d=0−m. Then every successive sample will correspond to the Brillouin backscatter generated at 2.8 m intervals assuming a 25 ns sampling interval. In general the waveform digitizer 26 repeatedly digitizes the intensity values of the return signal where each repetition corresponds to an optical signal generated at increasingly greater depths Thus a series of K values may be obtained for discrete depths on each probe beam pulse. Triggering processor 27 to begin its processing on the leading edge of such pulse enables it to convert the digital samples to K values and relate these to specific ocean depths. The conversion process will now be explained.

Data processor 27 is programmed to determine values of K from the relative Brillouin intensity readings at the output of digitizer 26 by making the following computations:

$$K_B = \frac{\ln[I_B(D_1)/I_B(D_2)] - \ln[(H + D_2)^2/(H + D_1)^2]}{2\Delta D} \quad (2)$$

where,
$I_B(D_1)$ = Brillouin signal at depth $D_1$;
$I_B(D_2)$ = Brillouin signal at depth $D_2$;
H = height of transmitter-receiver above the ocean surface;
$D_1$ and $D_2$ = two different depths;
$\Delta D = D_2 - D_1$;
ln = natural log;
$K_b$ = diffuse attenuation coefficient over the depth interval between $D_1$ and $D_2$.

One of the features of this measurement technique is that the computation process to ascertain K is independent of the output power of laser 12. So long as the output power of probe beam 18 is sufficient to generate backscattering from the desired ocean depths the beam can pass through variable attenuating media without affecting the measurements being made (provided that there is sufficient energy in the return backscatter to be detected by receiver optics 22). Another feature of this measurement technique is that it is amenable to various signal processing enhancements to improve the signal-to-noise ratio of the receiver, e.g. data processor 27 can digitally store and average a number of samples for noise improvement.

It should be noted that care should be taken to prevent over loading the receiver with either reflected light from the probe beam itself or from other forms of scattering in the water such as elastic scattering. One technique for reducing the effect of reflections off the water is to prevent their collection by directing probe beam 18 into the water a few degrees off nadir. Then, most reflections will be in a direction away from the airborne receiver. In addition as is evident to those skilled in the art, by proper timing of the return signals it is possible for the receiver to reject any reflections off the surface. Since reflections from each probe beam pulse occur immediately prior to the time the beam enters the water, it is important to trigger waveform digitizer 26 precisely at the time the backscatter signals start to arrive at the input to the digitizer In this way even though reflections may enter the receiver, they are rejected at the input to the waveform digitizer 26.

Figure 2:
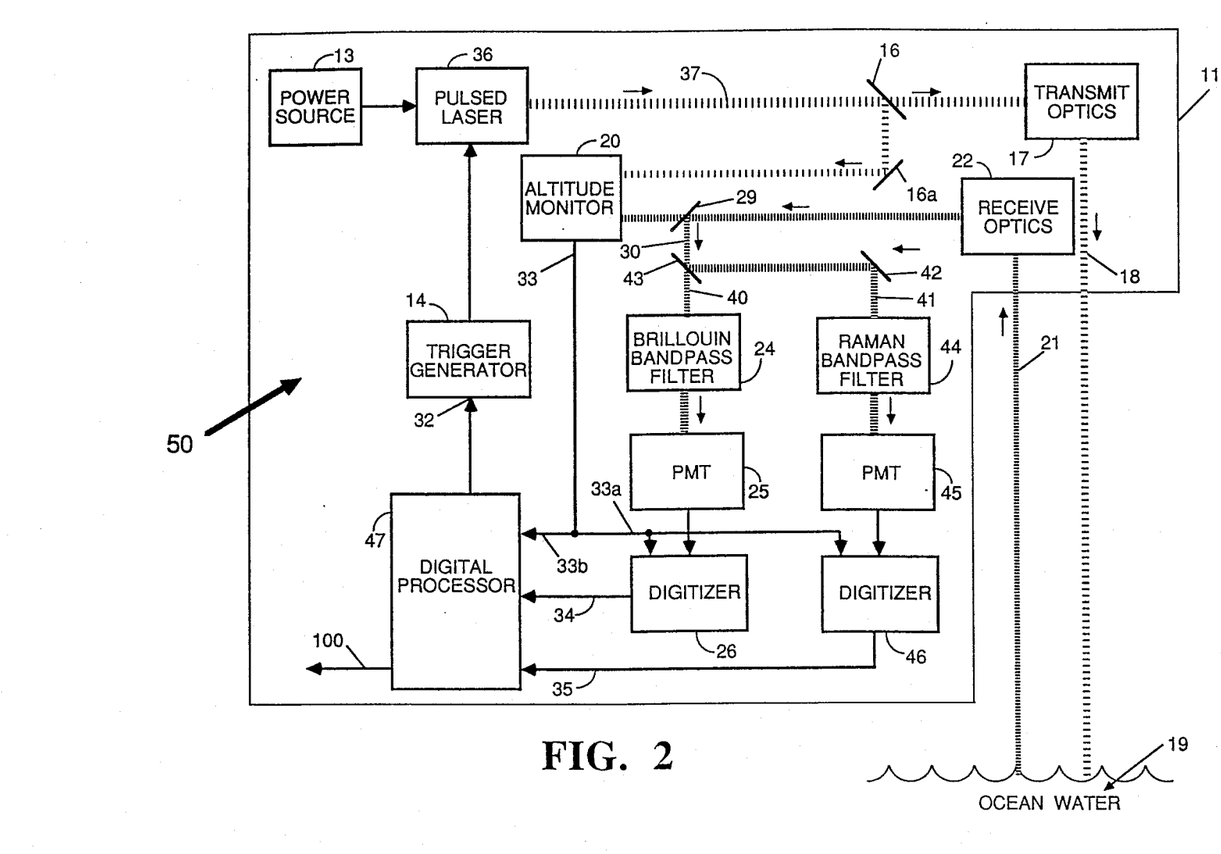
FIG. 2 is a block diagram of apparatus representing a modified form of the invention.

In addition to using light at the 532 nm (green) wavelength for submarine laser communication systems, light at the 455 nm (blue) wavelength is also practicable for this purpose. Accordingly it is desirable to survey K's in the world's oceans so that system performance estimates can be made accurately for these two wavelength systems. This is achievable by making surveys with two separate laser systems at the two wavelengths using the Brillouin apparatus and technique described above. It would be advantageous, however, and highly desirable to measure values of K simultaneously at these two wavelengths and to this end apparatus 50 shown in FIG. 2 is provided.

Apparatus 50 is similar in many respects to apparatus 10 of FIG. 1 and accordingly like reference characters indicate like parts on the drawings. Pulsed laser 36 produces a pulsed output 37 at a nominal 455 nm (blue) wavelength which is directed by transmitter optics 17 toward ocean 19. The linewidth of the laser output should be comparable to, or less than, the Brillouin scattering linewidth, i.e., 0.0004 nm, for highest performance. The blue light that enters the ocean water penetrates and interacts with it to produce both Brillouin (blue) and Raman (green) backscattering signals, a portion of which are received by receiver optics 22.

Figure 3:
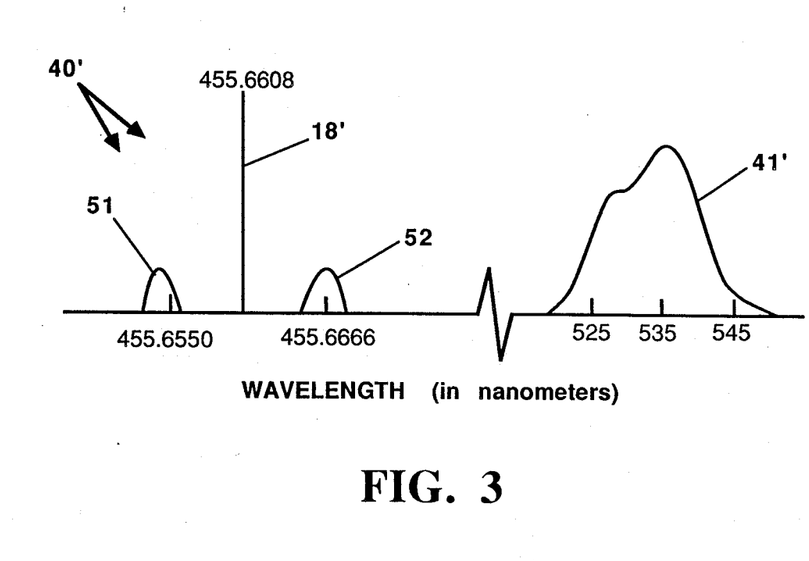
FIG. 3 is a frequency spectrum diagram showing representative spectra of backscattered signals and the probe beam signal.

FIG. 3 depicts the probe beam signal 18' and its wavelength and the Brillouin and Raman signals 40' and 41', respectively, and their wavelengths, as present at the output of beam splitter 43. The natural phenomena responsible for Raman and Brillouin scattering are very different. Raman scattering is a sideband of the incident light beam that is produced by a modulation of the dipole moment of the water molecule due to internal molecular vibration and rotation. Whereas, Brillouin scattering is caused by a doppler shift due to scattering from sound waves in the bulk fluid.

Referring again to FIG. 2, the output of receiver optics 22 is directed by partially reflecting mirror 29 to a dichroic beam splitter 43 which divides the return signals according to wavelength into a Raman signal at 41 and a Brillouin signal at 40. Obviously the selectivity of beam splitter 43 is insufficient to block the probe beam (18' in FIG. 3) and allow only the Brillouin signals to pass; that is the primary function of the Brillouin bandpass filter 24. The Brillouin signal 40, as described above, passes successively through its bandpass filter 24, PMT 25, and digitizer 26 to processor 27, the latter calculating the diffuse attenuation coefficient K at the blue Brillouin wavelength of 455 nm in accordance with equation (2) above. The Raman signal reflects off of mirror 42 and passes through its bandpass filter 44 centered at 532 nm, a PMT 45 similar to PMT 25, a digitizer 46 similar to digitizer 26 and finally to processor 47. Both waveform digitizers 46 and 26 are triggered by the same trigger pulse 33a from altitude monitor 20 so that the first digitized samples represent the Raman signal and the Brillouin signals at the ocean surface. Alternatively separate receive optics 22 could be used for the Raman and Brillouin signals.

In addition to being programmed to calculate K as defined by equation (2) at the Brillouin wavelength, processor 27 is also programmed to compute K at the Raman wavelength by making the following calculation:

$$K_R = \frac{\ln[I_R(D_1)/I_R(D_2)] - \ln[(H + D_2)^2/(H + D_1)^2] - K_B \Delta D}{\Delta D} \quad (3)$$

where, $I_R(D_1)$ = Raman signal at depth $D_1$;
$I_R(D_2)$ = Raman signal at depth $D_2$;
H, $D_1$, $D_2$ and $\Delta D$ are defined above;
$K_B$ = diffuse attenuation coefficient determined by Brillouin scattering over the depth interval $\Delta D$ from equation (2);
$K_R$ = diffuse attenuation coefficient at the Raman wavelength over the depth interval $\Delta D$.

Values of $K_R$ and $K_B$ for specific locations and depths can be either stored in memory (not shown) or output on a high speed digital line 100 for analysis. Such a system inherently generates a large amount of data very rapidly, and therefore, a suitable storage device is needed to hold the data.

In addition to using a Fabry-Perot interferometer, an alternate approach to the Brillouin signal filter 24 is an atomic resonance absorption filter using cesium gas as a component. Referring to FIGS. 2 and 3, laser 36 is tuned so that the unshifted blue laser line 18' is absorbed in the cesium while at least one of the Brillouin shifted lines 51 and 52 is not absorbed in the cesium and passes through filter 24. Additional details on the atomic resonance filter construction and principles of operation are described in an article entitled, "Atomic Resonance Filters" by J. A. Gelbwachs, *IEEE Journal of Quantum Physics*, Vol. 24, No. 7, July 1988, at Pp. 1266-1277 (see also the references cited therein at Pp. 1276-1277. Details on the specific atomic resonant filter used in the preferred embodiment are described infra.) If the O-H vibrational stretching transition of water is used as the Raman transition that is observed simultaneously with the Brillouin signal, the Raman measurement of K is placed at a wavelength band of 536±6 nm which includes the desired wavelength 532 nm. The O-H vibrational stretching transition vibrates at a frequency such that a primary laser wavelength of 455.6608 nm will exhibit a Raman sideband at 536±6 nm. Thus the use of a single laser 36 operating at a 455 nm wavelength enables measurement of K to be made simultaneously at 455 nm and 532 nm.

Figure 4:
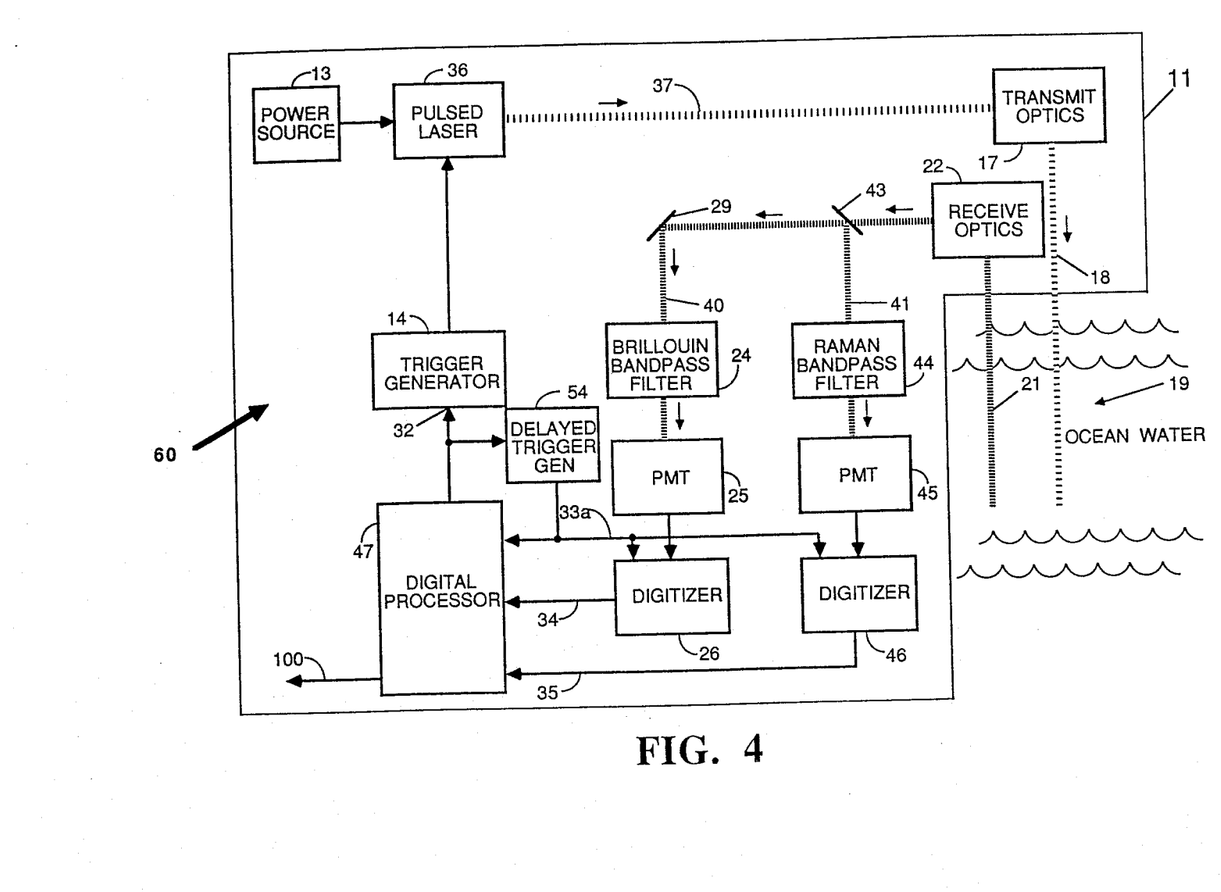
FIG. 4 is a block diagram of apparatus which is a modified form of the invention suitable for use on a submerged platform.

It will be seen from the above description that the practice of the subject invention permits remote operation as from an airborne platform, rapid operation resulting in a high area coverage rate at aircraft speeds, measurement of K at multiple depths, and measurement of K at two selected wavelengths simultaneously. It will be appreciated that the same techniques described are equally valid if, for some operational reasons, the platform is a surface vessel or submerged vessel. However certain advantages accrue practicing this invention from a submerged platform. For example, the maximum ocean depths which can be successfully probed from an airborne platform or a surface vessel are inherently less than operational depths of most submarines. Therefore, to probe the region below 100 m, the same basic technique would be useful if performed from a submerged submarine. Apparatus 60 depicted in FIG. 4 is suitable for this purpose.

Apparatus 60 is similar in many respects to apparatus 50 of FIG. 2 and accordingly like reference characters indicate like parts on the drawings. Referring to FIG. 4, apparatus 60 depicted therein is basically the same as apparatus 50 in FIG. 2, except that the altitude monitor 20 and the related optics have been replaced by a delayed trigger device 54 to trigger waveform digitizers 46 and 26. Since apparatus 60 is mounted in a submarine, the parameter H=0 since the water being probed is just a few centimeters from laser optics 17, and therefore, there is no need to calculate the altitude H. However, both waveform digitizers 46 and 26 still need to be triggered at the proper times. To this end they are triggered by the same trigger pulse 33a from delayed trigger generator 54 rather than the altitude monitor 20 shown in FIG. 2. This assures that both digitizers begin sampling as soon as the Raman and Brillouin signals 21 are generated and backscattered into the receiver optics 22. Since there is no appreciable separation between the receiver optics 22 and the ocean water the backscatter signals are immediately generated as soon as the probe beam exits the transmit optics 17. Therefore, the delayed trigger generator 54 is set to generate a pulse within a few microseconds of the trigger pulse firing laser 12. The exact delay time should be adjusted to compensate for the various delays in the system. (An oscilloscope connected to the output of the PMT's and the output of trigger generator 14 would be helpful in initially setting the proper delay time period.) Again this assumes that both digitizers 26 and 46 begin their sampling at the very start of the detected backscattered pulses. Processor 47 having the same trigger pulse input can relate the distance from the platform window to the digitized samples on digital paths 34 and 35.

Atomic Resonance Filter Assembly

A conventional atomic resonance filter (ARF) using cesium gas as the fluorescent material has three principal components: an initial red-blocking optical filter that passes only blue light; a cesium gas cell which absorbs at two-pairs of discrete blue wavelengths thus producing two near infra-red (NIR) output wavelengths; and a blue-blocking optical filter that passes only red light. In the conventional configuration the function of the second optical filter is to block any light passing through both the red-blocking input filter and the gas cell and to pass only that light which is absorbed and re-emitted in the NIR region in the cesium cell. The net effect is an extremely narrow (<0.010 nm) optical bandpass filter. The function being performed by filter 24 is somewhat different, and is therefore, a modified version of the standard atomic resonance filter.

The optical filter needed for this application is one that can separate one of the Brillouin side-band signals (51 or 52 in FIG. 3) from the much stronger signal (18' in FIG. 3). This is not a trivial task given the fact that the two signals are only 58 mÅ (0.0058 nm) apart and the Brillouin side bands are nearly 30 dB lower in strength than the unwanted signal 18'. The cesium filled ARF can separate these signals if certain changes are made to the conventional ARF. By tuning the wavelength of the probe beam to coincide with one of the lower pair of the cesium absorption lines, the cesium cell will upconvert the elastically scattered component (18') to the NIR region while leaving one of the desired Brillouin sideband signals unmodified. Then by replacing the standard red output filter with a second blue filter, the light component upconverted to NIR wavelengths in the cesium cell will be blocked and the unconverted blue light will pass out of the filter. So, instead of recovering the up-converted NIR photons, they are intentionally blocked. The resultant optical filter has a much broader passband with very narrow stopbands at four selective wavelengths. This solves the problem of separating the Brillouin lower side band (51 in FIG. 3) from the much stronger reflected probe beam signal or the elastically scattered component (18' in FIG. 3).

Figure 5:
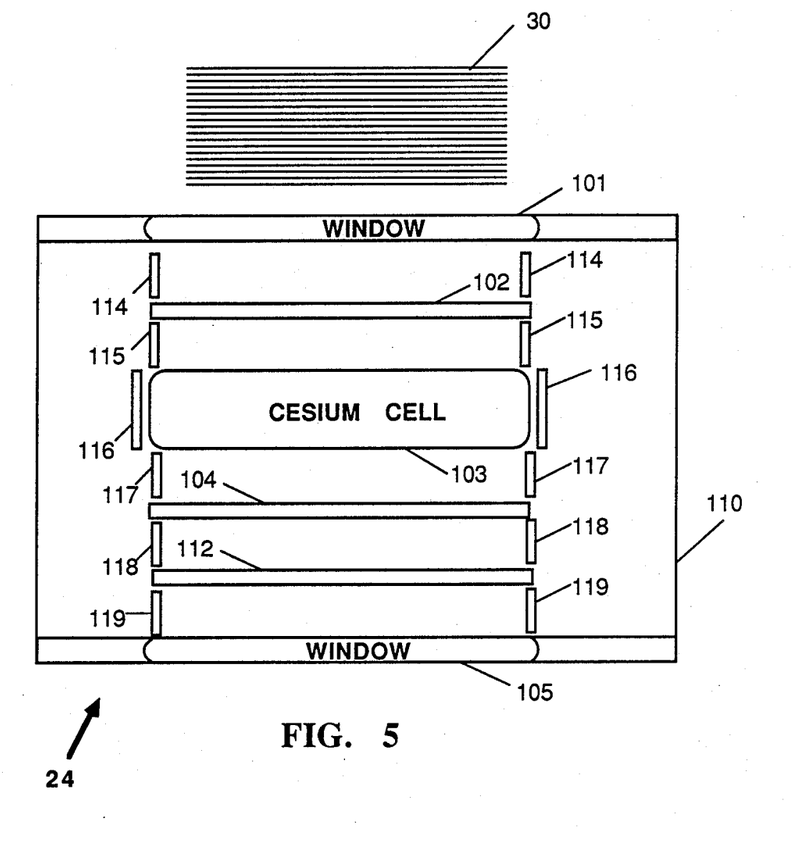
FIG. 5 is a schematic diagram of an atomic resonance filter employed in accordance with the present invention.

FIG. 5 is a schematic diagram showing greater functional detail of the modified atomic resonance filter assembly 24. The principal components of this ARF assembly are optical filters 102 and 104, and a cesium cell assembly 103. As explained above, the primary function of ARF assembly 24 is to selectively pass the desired Brillouin backscatter while substantially attenuating any reflected or elastically backscattered light at the same wavelength as the probe beam. Since atomic cesium has two sets of fixed absorption lines, one set at {455.6608 nm, 455.6546 nm} and another set at {459.4488 nm, 459.4424 nm}, the wavelength of the probe beam 18 is finely tuned to coincide with one of the shorter pair of these cesium absorption lines. Light beam 30 enters through window 101 and passes to optical filter 102. Both optical filters 102 and 104 are an absorptive type of optical broadband short-pass filter that allows photons in and around the cesium absorption profile of 455 nm to pass through the glass. The thickness of both filters 102 and 104 are chosen to optimize transmission at 455 nm while providing high attenuation at wavelengths of 700 nm to beyond 1000 nm. Only blue photons pass through to the cesium cell 103. The cesium cell 103 converts (fluoresces) the incoming photons at 455.6608 nm to NIR photons (at 852 nm and 894 nm). The second optical filter 104 is another short-pass filter designed to block the NIR photons generated in cell 103 and pass the Brillouin signal through to another heat shield 112. The combination of optical filters and cesium cell 702b provides at least 30 dB of attenuation to the unwanted 455.6608 nm or 455.6546 nm photons.

Sapphire heat shield 112 (approximately 0.25 in thick) reduces heat flow from the hot cesium cell 103 to the ensuing photo-detector. Blue reflectors 114-119 are placed around the circumference, above and below the cesium cell 103 to redirect high-angle incoming blue-signal photons downward. An enhanced aluminum reflective coating deposited on 5-mil thick kapton film is an effective relector, since it is sufficiently flexible to cover the interior chamber of the container 110. In the preferred embodiment, the cesium cell 103 uses a pyrex-type glass cylinder containing gaseous cesium at a low pressure of approximately 4 Torr with gaseous neon (a buffer gas) at a pressure of approximately 15 Torr. The cesium sublimes to the gaseous state when heated above approximately 30° Celsius The cell operates at a nominal temperature of 100° C. The vacuum fill point for the cell is designated as the "cold spot" of the cell. It functions as a cesium reservoir by maintaining its temperature at least 20° cooler than the rest of the cell. The temperature of the cold spot is controlled to maintain a specific gaseous cesium density inside the cell.

The cesium cell housing contains two heaters (not shown in FIG. 5), one for the cell side (edge) and the other for the cold spot. The heaters are controlled by closed-loop servo circuitry (also not shown). Thermal sensors at the cell edge, cold spot, and center provide analogs of these temperatures to temperature control circuitry. The cesium cell 103 is heated to approximately 100° C. and the vapor pressure is accurately controlled to optimize the cell performance. The space between the outer side wall of the cesium cell and the cell heaters should be coated with a suitable reflective paint or compound to reflect the blue wavelengths or packed with a reflective powder to optimize the filters performance. The side walls form a part of an integrating sphere around the cesium cell 103. This assembly reflects both the NIR and blue signal light from the top and side portions of the light chamber back into the cesium cell, while thermally isolating the cesium cell assembly from its environmental enclosure 110.

Post-cell filter 104 is designed generally to attenuate ambient sunlight and the converted blue wavelengths while allowing the nonconverted blue signal photons to pass through to PMT detector 25. Filter 104 also acts as a radiative heat shield to attenuate thermal radiation from cell 103. The primary purpose of heat shield 118 is to absorb the thermal radiation from the cesium cell which remains after passing through the red filter 104. Before filter 24 can be operated, all water vapor must be removed from the pressure vessel 110. This is done by purging the entire chamber with dry nitrogen. For additional details on ARF's refer to *MILCOM 87 Proceedings*, "Atomic Resonance Filter Optical Receiver (ARFORM) Module," by Paul Titterton and James F. Shaw, No. 25.1, Oct. 21, 1987.

The desired blue wavelengths pass out through the exit window 105 to the PMT assembly 25 (shown in FIG. 4) for conversion to an electrical pulse signal.

Fabry-Perot Interferometric Filtering

Figure 6:
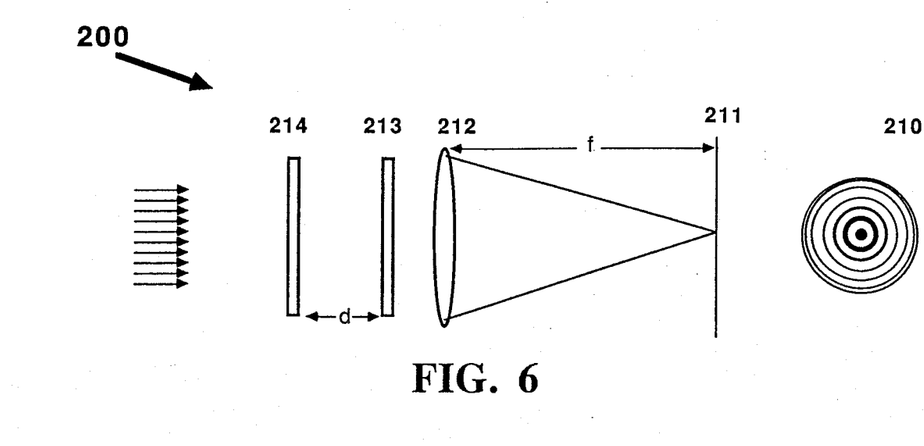
FIG. 6 is a schematic diagram of a plano Fabry-Perot interferometer in the presence of monochromatic light.

Referring to FIG. 6, using a plano Fabry-Perot interferometer 200 in the presence of monochromatic light impinging upon partially reflective flat parallel mirrors 213 and 214, and focussed by convex lens 212 an optical pattern of concentric circles 210 is produced in the image plane 211. The radii of the rings 210, as shown in *Fabry-Perot Interferometer*, by G. Hernandez, Cambridge University Press 1986, (eqn. 2.1.8) is:

$$V_m = f \cos^{-1} \frac{m\lambda}{2d} \quad (4)$$

where, $V_m$ is the radius of the $m^{th}$ ring;
f is the focal length of lens 212;
m is an integer;
$\lambda$ is the wavelength of incident light; and
d is the spacing between the plane parallel mirrors 213 and 214

With additional wavelengths present, additional rings will appear between the original rings. If the incident light field is the elastic scattering (unshifted) components, the ring pattern 210 shown in FIG. 6 is formed. The Brillouin stokes 82 and antistokes 83 components (shown in FIG. 8), having been shifted in wavelength, produce additional rings in the image plane 211 of FIG. 6.

Figure 7:
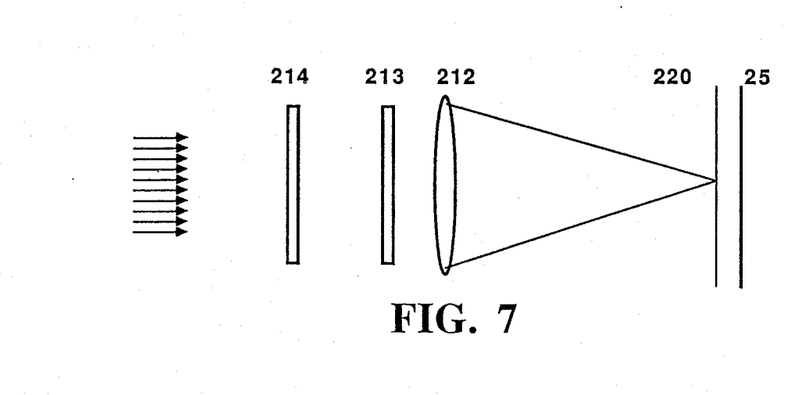
FIG. 7 is a schematic diagram of a modified plano Fabry-Perot interferometer in accordance with the present invention; and, FIG. 8 is a line diagram showing the radial positions of the unshifted and shifted wavelengths formed at the image plane of a Fabry-Perot interferometer.
Figure 8:
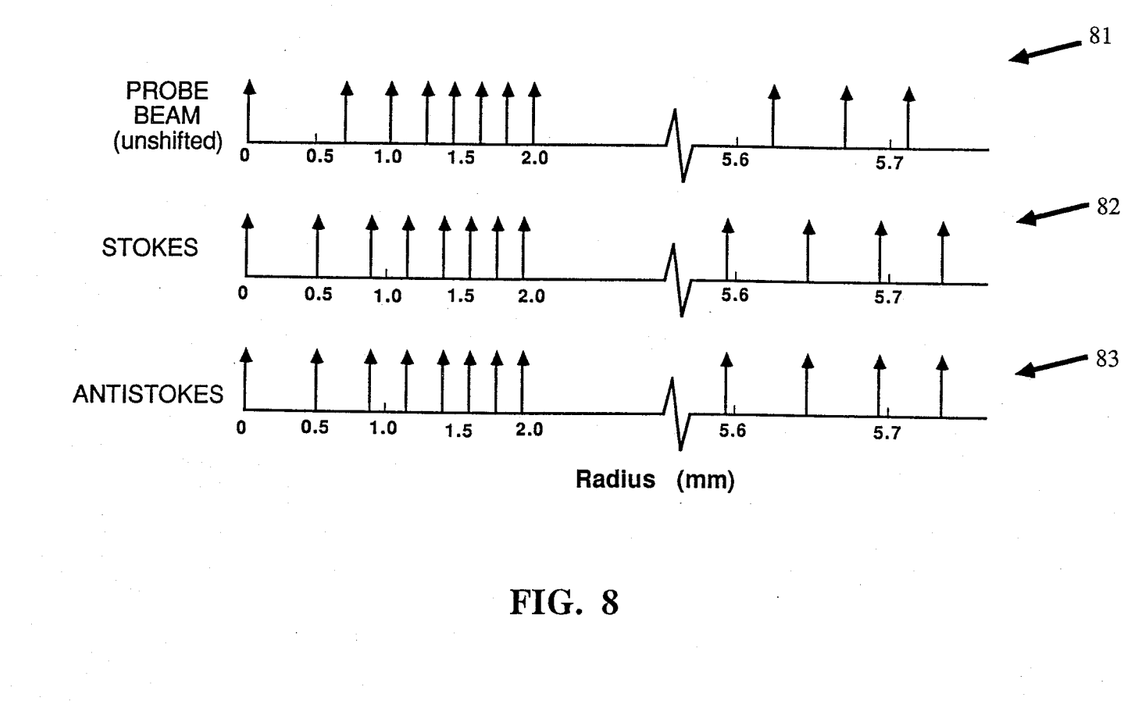

Referring to FIGS. 7 and 8, to be able to reject the unshifted components 81 and yet admit the shifted Brillouin components 82 and 83, mask 220 is employed. Mask 220 has opaque rings coinciding with the ring pattern of the unshifted components with transparent regions between these rings to permit the Brillouin components to pass through to the photodetector 25. With a properly designed interferometer, the rings produced by the shifted Brillouin components 81 can be made to fall midway between the unshifted rings 82 and 83, as shown in FIG. 8. For example with a 532 nm probe beam, the stokes and antistokes Brillouin components at water temperatures within the range of 5° to 50° C. will be near 532.007 nm and 531.993 nm respectively. Using an interferometer spacing "d" of 1.011065 cm, the radii of the shifted (82 and 83) and unshifted components 81 are as shown in FIG. 8. The stokes and antistokes components (82 and 83) occupy identical positions with the unshifted components 81 midway between. This permits the use of mask 220 to block out the unshifted components without interrupting the shifted component. Mask 220 can easily be constructed to exactly match the interferometer by exposing a photographic plate in the image plane 211 when only the unshifted component is present. The developed negative will serve directly as the mask.

To improve the etendue or throughput of the interferometer-based receiver, an integrating sphere may be used before the interferometer 200. Those input rays that do not contribute to the ring pattern will be reflected back into the integrating sphere where their angles are scrambled and redirected at a proper angle into the interferometer. See U.S. Pat. No. 4,907,887 entitled, "High Resolution Interferometer with High Etendue," filed on Nov. 10, 1988.

While the invention has been described with reference to its preferred embodiment, it will be understood by those skilled in the art that various changes may be made and equivalents may be substituted for elements thereof without departing from the true spirit and scope of the invention. In addition, many modifications may be made to adapt a particular situation or material to the teaching of the invention without departing from its essential teaching. To this end it may be advantageous to mount apparatus 17 in FIG. 2 on a two-axis gimbal to sweep the probe beam from side to side lateral to the direction of flight of the airborne platform. This would enable a much wider area to be covered by the moving platform than by simply directing the beam in a downward direction.

What is claimed is

1. Apparatus for measuring the diffuse attenuation coefficient of ocean water comprising:
   pulsed laser means for producing a pulsed output beam having a wavelength $\lambda_o$;
   optical transmitter means positioned above said ocean water for directing said pulsed output beam as a probe beam into said ocean water, said probe beam interacting with said ocean water and producing at least Brillouin backscatter signals at the wavelength $\lambda$ where, $\lambda_o \neq \lambda_1$, propagating generally oppositely to the direction of propagation of said probe beam; and,
   optical receiver means positioned above said ocean water for receiving said backscatter signals and for generating therefrom the diffuse attenuation coefficients of said ocean water at the wavelength $\lambda_1$.

2. Apparatus according to claim 1 wherein said optical receiver means further generates said diffuse attenuation coefficient at the wavelength $\lambda_1$ at multiple ocean depths.

3. Apparatus according to claim 2 wherein said apparatus is mounted on an airborne platform spaced above and movable over said ocean surface.

4. Apparatus for measuring the diffuse attenuation coefficient of ocean water comprising:
   a pulsed laser having an energizing power source and capable of producing a pulsed output beam;
   optical transmitter means positioned above said ocean water for receiving said output beam and for directing same as a probe beam into said ocean water, said probe beam interacting with said ocean water and producing Brillouin and Raman backscatter signals at Brillouin and Raman wavelengths, respectively, propagating generally oppositely to the direction of propagation of said probe beam;
   optical receiver means positioned above said ocean water for receiving said backscatter signals and for producing optical output signals containing said Brillouin and Raman signals;
   first filter means receiving said optical output signals of said receiver means and passing only said Brillouin signals;
   second filter means receiving said optical output signals of said receiver means and passing only said Raman signals;
   first and second photodetector means receiving said Brillouin and Raman signals, respectively, and converting same to respective electrical signals; and
   processor means responsive to said respective electrical signals and computing therefrom the diffuse attenuation coefficients of said ocean water at the Brillouin and Raman wavelengths, respectively.

5. Apparatus according to claim 4 and further comprising:

first and second digitizer means for receiving said Brillouin and Raman electrical signals, respectively, and for converting same into respective digital signals; and said processor means being a digital processor for receiving said respective digital signals and rapidly computing therefrom the diffuse attenuation coefficient of said ocean water at the Brillouin and Raman wavelengths.

6. Apparatus according to claim 5 wherein said first and second digitizer means have means for selectively sampling and digitizing said Brillouin and Raman electrical signals at predetermined intervals and thereby passing to said digital processor Brillouin and Raman signals from selected depths in said ocean water.

7. Apparatus according to claim 6 and further comprising.

altitude monitor means responsive to both said pulsed output beam from said pulsed laser and said optical output signals from said receiver means for producing a timing signal corresponding to the distance between said transmitter/receiver means and the surface of said ocean water and means for transmitting said timing signal to said first and second digitizer means and to said processor means, the difference between the occurrence of said timing signal and the time of operation of said digitizer means corresponding to the water depth at which said Brillouin and Raman signals originate.

8. Apparatus according to claim 4 mounted in an aircraft spaced above and movable over said ocean water.

9. Apparatus for measuring the diffuse attenuation coefficient of ocean water, said apparatus being mounted on a platform above the ocean surface and comprising:

pulsed laser means for producing a pulsed output beam having a wavelength $\lambda_o$;

optical transmitter means for directing said pulsed output beam as a probe beam into said ocean water, said probe beam interacting with said ocean water and producing elastically scattered unshifted signals and inelastic optical backscattering signals at a wavelength $\lambda_1$, both propagating generally oppositely to the direction of propagation of said probe beam;

optical receiver means mounted on said platform for receiving said backscattering signals and for producing optical output signals containing same;

optical bandpass filter means for receiving said optical output signals and for passing a very narrow bandwidth of signals including said optical backscattering signals at said $\lambda_1$ wavelength and blocking elastically scattered unshifted signals;

photodetector means for receiving said filtered optical backscattering signals and for converting same to corresponding electrical signals; and, processor means responsive to said electrical signals for computing therefrom the diffuse attenuation coefficient of said ocean water at said $\lambda_1$ wavelength.

10. Apparatus according to claim 9 further comprising a waveform digitizer for coupling said electrical signals to said processor means, and for periodically converting same into corresponding digital signals.

11. Apparatus according to claim 10 wherein said platform further comprises an aircraft spaced above and movable over said ocean surface.

12. Apparatus according to claim 11 wherein said optical bandpass filter means further comprises an atomic resonant filter having a stop band at the wavelength of said pulsed output beam.

13. Apparatus according to claim 11 wherein said optical bandpass filter means further comprises a plano Fabry-Perot interferometer in series with a optical interference prefilter centered at the wavelength of said pulsed output beam.

14. Apparatus according to claim 11 in which said pulsed output beam wavelength $\lambda_o$ is equal to 532 nm, said inelastic backscattering signals being Brillouin signals.

15. Apparatus according to claim 10 wherein said platform further comprises a ship on said ocean surface.

16. Apparatus for measuring the diffuse attenuation coefficient of ocean water, said apparatus being mounted on an airborne platform travelling above the ocean surface and comprising:

pulsed laser means for producing a pulsed output beam having a wavelength $\lambda_o$;

optical transmitter means for directing said pulsed output beam as a probe beam into said ocean water, said probe beam interacting with said ocean water and producing Brillouin and Raman backscatter signals at Brillouin and Raman wavelengths $\lambda_1$ and $\lambda_2$, respectively, propagating generally oppositely to the direction of propagation of said probe beam;

optical receiver means mounted on said platform for receiving said Brillouin and Raman backscattering signals and for producing optical output signals containing same;

first optical bandpass filter means for receiving said optical output signals and for passing a very narrow bandwidth of first filtered backscatter signals including said optical backscattering signals at said $\lambda_1$ wavelength;

second optical bandpass filter means for receiving said optical output signals and for passing a very narrow bandwidth of second filtered backscatter signals including said optical backscattering signals at said $\lambda_2$ wavelength;

first photodetector means for receiving said first filtered backscatter signals and for converting same to first corresponding electrical signals;

second photodetector means for receiving said second filtered backscatter signals and for converting same to corresponding second electrical signals;

first digitizer means for receiving said first electrical signals and for periodically converting same into a series of first digital signals, each such series corresponding to the intensity values of the Brillouin backscatter signals generated at discrete depths beneath the ocean surface;

second digitizer means for receiving said second electrical signals and for periodically converting same into a series of second digital signals, each such series corresponding to the intensity values of the Raman backscatter signals generated at discrete depths beneath the ocean surface; and, processor means responsive to said series of first and second digital signals, electrical signals for computing therefrom the diffuse attenuation coefficient of said ocean water at said $\lambda_1$ and $\lambda_2$ wavelengths.

* * * * *